(12) United States Patent
Qin et al.

(10) Patent No.: US 7,476,556 B2
(45) Date of Patent: Jan. 13, 2009

(54) SYSTEMS AND METHODS FOR PLASMA PROCESSING OF MICROFEATURE WORKPIECES

(75) Inventors: Shu Qin, Boise, ID (US); Allen McTeer, Eagle, ID (US)

(73) Assignee: Micron Technology, Inc., Boise, ID (US)

( * ) Notice: Subject to any disclaimer, the term of this patent is extended or adjusted under 35 U.S.C. 154(b) by 254 days.

(21) Appl. No.: 11/201,668

(22) Filed: Aug. 11, 2005

(65) Prior Publication Data

US 2007/0037300 A1 Feb. 15, 2007

(51) Int. Cl.
*H01L 21/66* (2006.01)
*H01L 21/00* (2006.01)

(52) U.S. Cl. .................. 438/16; 438/8; 438/9; 438/14; 257/E21.218; 257/E21.143

(58) Field of Classification Search .................. 438/8, 438/9, 14, 16; 257/E21.143, E21.218
See application file for complete search history.

(56) References Cited

U.S. PATENT DOCUMENTS

| | | | |
|---|---|---|---|
| 6,265,831 B1 * | 7/2001 | Howald et al. ......... 315/111.21 |
| 6,800,562 B1 * | 10/2004 | Cusson et al. ............... 438/714 |
| 7,329,549 B2 * | 2/2008 | Saito .............................. 438/9 |
| 2003/0082838 A1 * | 5/2003 | Petrucci et al. ................ 438/14 |
| 2004/0007326 A1 * | 1/2004 | Roche et al. ........... 156/345.24 |
| 2005/0034811 A1 * | 2/2005 | Mahoney et al. ....... 156/345.24 |

OTHER PUBLICATIONS

Qin, S. et al., "The Response of a Microwave Multipolar Bucket Plasma to a High Voltage Pulse," IEEE Transactions on Plasma Science, vol. 19, No. 6, pp. 1272-1278, Dec. 1991.
Qin, S. et al., "Charge Transfer Cross Section of $He^+$ in Collisional Helium Plasma Using the Plasma Immersion Ion Implantation Technique," Journal of Applied Physics, vol. 74, No. 3, pp. 1548-1552, Aug. 1993.

* cited by examiner

*Primary Examiner*—Charles D Garber
*Assistant Examiner*—Seahvosh J Nikmanesh
(74) *Attorney, Agent, or Firm*—Perkins Coie LLP

(57) ABSTRACT

Systems and methods for plasma processing of microfeature workpieces are disclosed herein. In one embodiment, a method includes generating a plasma in a chamber while a microfeature workpiece is positioned in the chamber, measuring optical emissions from the plasma, and determining a parameter of the plasma based on the measured optical emissions. The parameter can be an ion density or another parameter of the plasma.

25 Claims, 4 Drawing Sheets

SYSTEMS AND METHODS FOR PLASMA PROCESSING OF MICROFEATURE WORKPIECES

TECHNICAL FIELD

The present invention is directed to systems and methods for plasma processing of microfeature workpieces.

BACKGROUND

Plasma-based processes, such as plasma enhanced physical vapor deposition, plasma enhanced chemical vapor deposition, plasma etching, plasma immersion ion implantation, and conventional ion implantation, are used in the manufacturing of workpieces having microfeatures. During plasma processes, the plasma density and other plasma parameters must be tightly controlled to produce workpieces within specification. For example, the implant dose of an ion implanter depends on the ion density of the ion source, and the film deposition rate of a physical vapor deposition tool also depends on the ion density.

Conventional devices for measuring plasma parameters include a Langmuir probe. For example, FIG. 1 schematically illustrates a conventional plasma processing system 1 with a Langmuir probe 20. The system 1 further includes a processing vessel 2, a microwave transmitting window 4, and a microwave generator 6. The microwave generator 6 has a wave guide 8 and an antenna 10 positioned so that microwaves radiated by the antenna 10 propagate through the window 4 and into the processing vessel 2 to produce a plasma. The Langmuir probe 20 is inserted into the vessel 2 between process steps to measure plasma parameters. Specifically, a voltage is applied to the probe 20 and scanned from negative to positive while the current is measured. The plasma parameters can be extracted from the relationship between the voltage and current. For example, the ion density can be determined from the ion saturation current (also called a Bohm current $I_B$) when the scanning voltage is negative. Specifically, the ion density $n_i$ can be calculated by the following equation when the scanning voltage is negative:

$$n_i = \frac{2}{q} \frac{I_B}{A_{eff}} \sqrt{\frac{M_{eff}}{kT_e}}$$

in which $I_B$ is the ion saturation current collected by the probe 20 under a negative voltage, q is the ion or electron charge, $A_{eff}$ is the effective area of the probe 20, $kT_e$ is the electron temperature in units of eV, and $M_{eff}$ is the effective ion mass.

The electron density, which should be generally equal to the ion density in a quiescent plasma, can be calculated from the electron saturation current when the scanning voltage is positive. Specifically, the electron density $n_e$ can be calculated by the following equation when the scanning voltage is positive:

$$n_e = \frac{2}{q} \frac{I_{esat}}{A_{eff}} \sqrt{\frac{M_e}{kT_e}}$$

in which $I_{esat}$ is the electron saturation current collected by the probe 20 when the positive scanning voltage equals the plasma potential $V_P$, q is the ion or electron charge, $A_{eff}$ is the effective area of the probe 20, $kT_e$ is the electron temperature in units of eV, and $M_e$ is the electron mass. The electron temperature $T_e$ and the plasma potential $V_P$ can be determined from the slope of the electron current and the knee of the electron saturation current, respectively.

One drawback of the Langmuir probe is that the probe cannot measure the plasma parameters in situ and in real time during processing because the probe interferes with the plasma. Specifically, the probe introduces contamination into the vessel and obstructs ingress and egress of the workpiece from the vessel. Another drawback of the Langmuir probe is that the probe cannot measure nonequilibrium plasma such as pulsed glow discharge or steady state plasma With a high voltage pulse. During pulsed plasma processes, the dynamic sheath of the plasma expands and may touch the probe if the probe is too close to the cathode. Therefore, the plasma parameters cannot be measured properly. Another issue is that during the high voltage pulse, the secondary electrons emitted from the cathode can be collected by the probe, which alters the current-voltage characteristics.

Yet another drawback of the Langmuir probe is the measurements can be inaccurate for several reasons. First, the probe draws current from the plasma, which causes significant perturbation in the plasma. Second, if the system includes a radio-frequency generator or magnetron assembly, the radio-frequency or magnetic interference can affect the measurements. Third, the measurements can be affected by sputtering, etching, and/or deposition phenomena depending on the plasma species and process conditions. Fourth, the probe does not measure the parameters of the plasma during workpiece processing, but rather before and/or after processing the workpiece. Accordingly, there is a need to improve the process of measuring plasma parameters.

DETAILED DESCRIPTION

A. Overview

Figure 1:
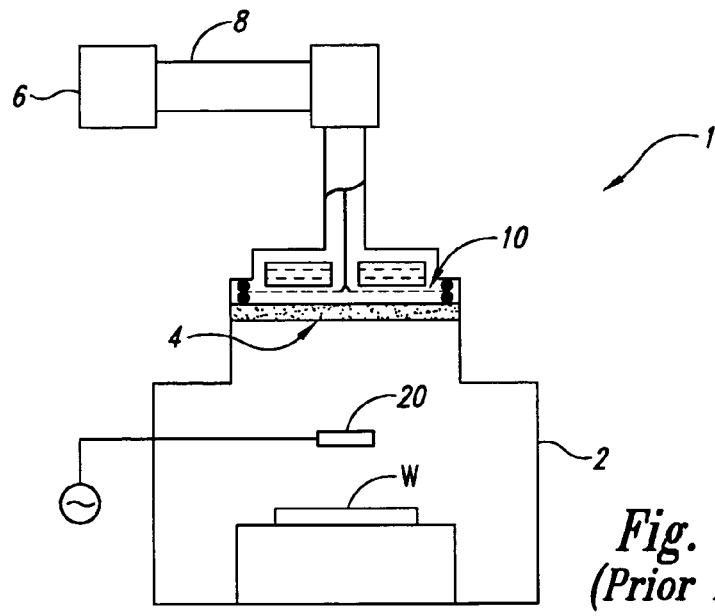
FIG. 1 schematically illustrates a conventional plasma processing system with a Langmuir probe.

The following disclosure describes various embodiments of systems and methods for plasma processing of microfeature workpieces. Several embodiments of such systems and methods monitor the plasma in situ while processing a workpiece without contaminating or otherwise affecting the plasma. Several embodiments of systems and methods in accordance with the invention can provide information regarding the ion density or other parameters of the plasma for controlling the plasma process An embodiment of one method in accordance with the invention includes generating a plasma in a chamber while a microfeature workpiece is positioned in the chamber, measuring optical emissions from the plasma, and determining a parameter of the plasma based on the measured optical emissions. The parameter can be an ion density, an electron density, or another parameter of the plasma. Measuring optical emissions from the plasma may include (a) determining an intensity of the optical emissions at a plurality of wavelengths from a first region of the plasma spaced apart from the microfeature workpiece by a first distance, and (b) determining an intensity of the optical emissions at a plurality of wavelengths from a second region of the plasma spaced apart from the microfeature workpiece by a second distance different than the first distance.

In another embodiment, a method includes generating a plasma in a chamber, depositing material onto a microfeature workpiece in the chamber, and monitoring in real time a parameter of the plasma in the chamber while depositing material onto the microfeature workpiece. The material can be deposited onto the workpiece by plasma enhanced atomic layer deposition (ALD), plasma enhanced chemical vapor deposition (CVD), plasma etching, plasma immersion ion implantation, conventional ion implantation, and/or other processes. Monitoring the parameter of the plasma can include measuring optical emissions from the plasma and estimating a dimension of a sheath of the plasma based on the optical emissions.

Another aspect of the invention is directed to systems for processing microfeature workpieces. In one embodiment, a system includes a plasma chamber coupleable to a source of gas, a workpiece support positioned within the plasma chamber and configured to carry a microfeature workpiece, an energy source positioned to generate a plasma within the plasma chamber, and a detector positioned external to the plasma chamber for measuring optical emissions from the plasma in the plasma chamber. The detector may include an optical emissions spectrometer and a sensor head operably coupled to the spectrometer. The sensor head can be movable relative to the plasma chamber.

In another embodiment, a system includes a plasma chamber, an energy source positioned to impart energy to atoms within the plasma chamber, a detector for measuring optical emissions from a plasma in the plasma chamber, and a controller operably coupled to the detector and configured to monitor in real time a parameter of the plasma based at least in part on a signal received from the detector while processing a microfeature workpiece in the chamber. The controller can include a computer-readable medium having instructions to perform one or more of the above-noted methods.

Many specific details of the invention are described below with reference to systems for depositing materials onto microfeature workpieces, which specifically include implanting or otherwise introducing ions and/or other materials into workpieces. The term "microfeature workpiece" is used throughout to include substrates upon which and/or in which microelectronic devices, micromechanical devices, data storage elements, read/write components, and other features are fabricated. For example, microfeature workpieces can be semiconductor wafers (e.g., silicon or gallium arsenide wafers), glass substrates, insulative substrates, and many other types of materials. The microfeature workpieces typically have submicron features with dimensions of a few nanometers or greater. Furthermore, the term "gas" is used throughout to include any form of matter that has no fixed shape and will conform in volume to the space available, which specifically includes vapors (i.e., a gas having a temperature less than the critical temperature so that it may be liquefied or solidified by compression at a constant temperature). Several embodiments in accordance with the invention are set forth in FIGS. 2-7 and the following text to provide a thorough understanding of particular embodiments of the invention. A person skilled in the art, however, will understand that the invention may have additional embodiments, or that the invention may be practiced without several of the details of the embodiments shown in FIGS. 2-7.

Figure 2:
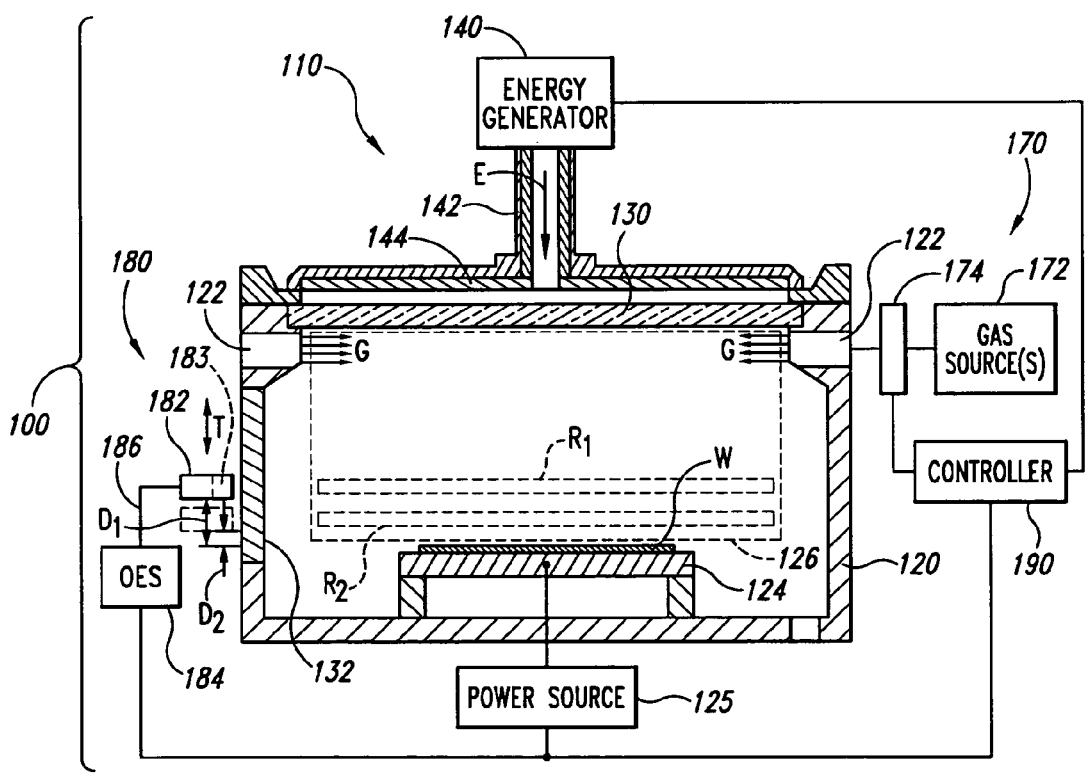
FIG. 2 is a schematic cross-sectional view of a plasma deposition system for processing a microfeature workpiece in accordance with one embodiment of the invention.

B. Embodiments of Plasma Deposition Systems for Fabricating Microfeatures on Workpieces FIG. 2 is a schematic cross-sectional view of a plasma deposition system 100 for processing a microfeature workpiece W in accordance with one embodiment of the invention. The illustrated plasma deposition system 100 includes a reactor 110, a gas supply 170 for providing gases to the reactor 110, a detector 180 for determining a parameter of a plasma in the reactor 110, and a controller 190 (shown schematically) containing computer operable instructions for controlling the processing of the workpiece W in the reactor 110. The deposition system 100 can perform plasma enhanced atomic layer deposition (ALD), plasma enhanced chemical vapor deposition (CVD), plasma etching, plasma immersion ion implantation, conventional ion implantation, and/or other processes.

The illustrated reactor 110 includes a chamber 120, a gas distributor 122 in fluid communication with the gas supply 170, a workpiece support 124 for holding the workpiece W in the chamber 120, a power source 125 (shown schematically) for applying an electrical bias, including DC, DC pulse, RF, or other voltage to the workpiece W, and a window 130 transmissive to plasma energy. The gas distributor 122 can be an annular antechamber having a plurality of ports for injecting or flowing gases G into the chamber 120. More specifically, the gas distributor 122 can be a manifold having a plurality of different conduits so that individual gases are delivered through dedicated ports. The window 130 can be a plate or pane of material through which energy propagates into the chamber 120 to generate a plasma in a plasma zone 126. The window 130 accordingly has a high transmissivity to the plasma energy that generates the plasma. For example, when microwave energy is used to generate the plasma, the window 130 can be a quartz plate or other material that readily transmits microwaves.

The reactor 110 further includes an energy system having a generator 140 (shown schematically) for generating a plasma energy, an energy guide 142 coupled to the generator 140, and an antenna 144 or other type of transmitter coupled to the energy guide 142. The generator 140 can generate microwave, radio-frequency, or other suitable types of radiation. For example, the generator 140 can produce microwave energy at 2.45 GHz or another frequency suitable for producing a plasma in the plasma zone 126. The generator 140 generates a plasma energy E that propagates through the energy guide 142 to the antenna 144, and the antenna 144 transmits the plasma energy E through the window 130 to the plasma zone 126.

The gas supply 170 includes one or more gas sources 172 for containing or producing process gases and a valve assembly 174 for regulating the flow of gas to the chamber 120. For example, in several CVD and ALD applications, the gas sources 172 include a first precursor gas source, a second precursor gas source, and a purge gas source. The first and second precursors are the gas and/or vapor constituents that react to form the thin, solid layer on the workpiece W during CVD and ALD processes. In other applications, the gas supply 170 may include an etchant gas source and/or a dopant gas source.

The controller 190 generates signals to operate the valve assembly 174 and control the flow of gas into the chamber 120. For example, in a CVD process, the controller 190 operates the valve assembly 174 to inject first and second process gases into the plasma zone 126 concurrently. The first and second process gases can be mixed in the gas distributor 122 or in the plasma zone 126. In an ALD process, the controller 190 operates the valve assembly 174 to inject discrete pulses of the first and second process gases into the plasma zone 126 at separate times. The plasma is generated from one or both of the first and second process gases to form a material on the workpiece W. In etching, ion implantation, and other suitable processes, the controller 190 operates the valve assembly 174 to regulate the flow of the corresponding gases into the chamber 120.

The detector 180 is positioned adjacent to the chamber 120 and determines one or more parameters of the plasma in the plasma zone 126. Specifically, the illustrated of the plasma based on the measured optical emissions. For example, the detector 180 can determine an ion density, an electron density, and/or various other parameters of the plasma. The illustrated detector 180 includes a sensor head 182 adjacent to a window 132 in the reactor 110, an optical emissions spectrometer 184 (shown schematically), and optical fibers 186 coupling the sensor head 182 to the spectrometer 184. The illustrated sensor head 182 is positioned to have a direct line of sight through the window 132 to the plasma zone 126, and can be movable along the window 132 in a direction T to sense optical emissions from various regions of the plasma zone 126. The sensor head 182 may also include a collimator 183 so that the detector 180 measures emissions from only a desired region of the plasma zone 126. The optical emissions spectrometer 184 measures the intensity of the optical emissions and may include a controller for determining one or more parameters of the plasma based on the measured intensity. Alternatively, the controller 190 can determine one or more parameters of the plasma based on signals from the optical emissions spectrometer 184. In other embodiments, the detector 180 may not include the sensor head 182 and/or the optical fibers 186, but rather the optical emissions spectrometer 184 can be positioned adjacent to the window 132. In additional embodiments, the detector 180 may include a camera such as a video camera.

C. Embodiments of Methods for Determining a Parameter of a Plasma

Figure 3:
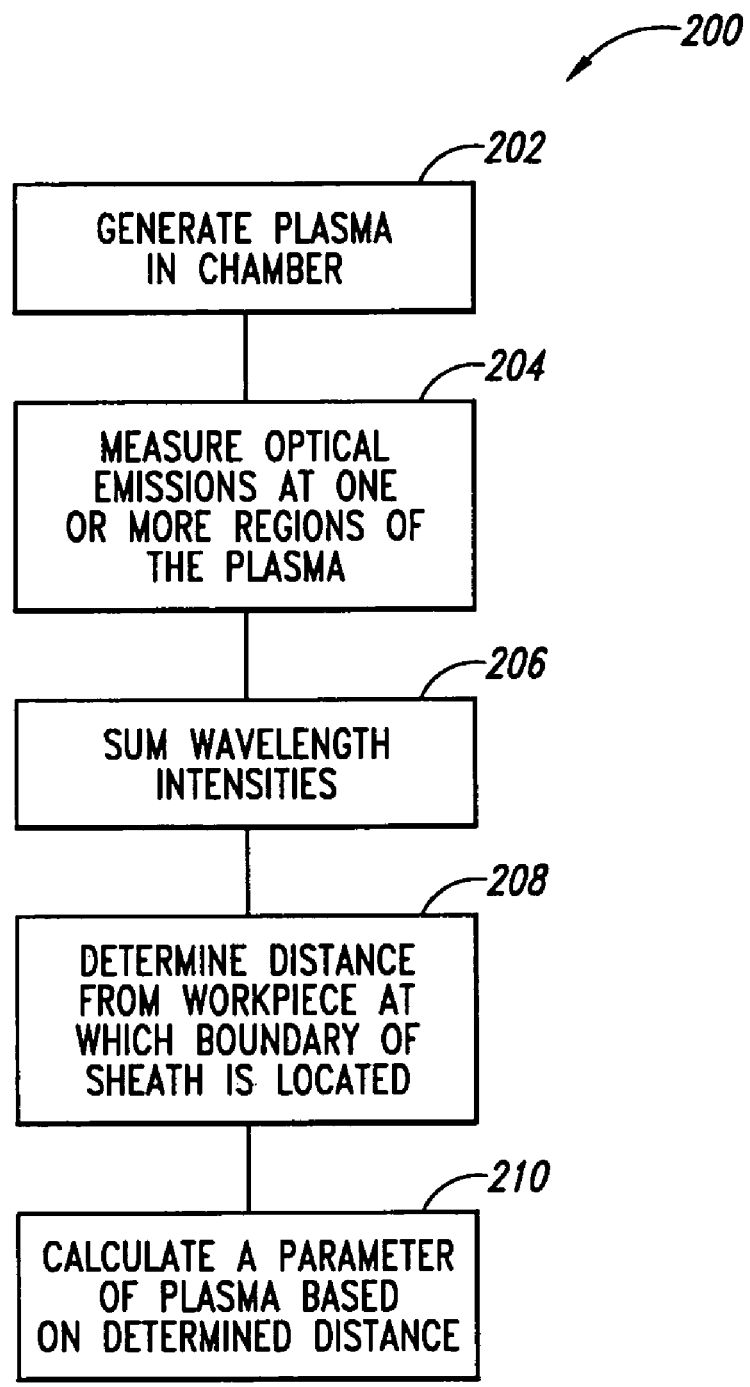
FIG. 3 is a flow chart of a method for determining a parameter of a plasma in accordance with one embodiment of the invention.

FIG. 3 is a flow chart of a method 200 for determining a parameter of a plasma in accordance with one embodiment of the invention. The illustrated method 200 includes a generating plasma procedure 202, a measuring procedure 204, a first calculating procedure 206, a determining procedure 208, and a second calculating procedure 210. These procedures can be performed by the system 100 shown in FIG. 2. The operation of the system 100 shown in FIG. 2 in accordance with the method 200 shown in FIG. 3 enables the system 100 to determine, monitor, and/or control one or more plasma parameters during processing to produce advanced workpieces that have very small feature sizes and high densities of features. Several embodiments of these procedures will be discussed below with reference to the system 100 of FIG. 2.

One embodiment of the generating plasma procedure 202 includes generating a plasma from a gas injected into the plasma zone 126 of the chamber 120. For example, the controller 190 can cause the valve assembly 174 to inject a process gas into the plasma zone 126 via the gas distributor 122 while the generator 140 generates energy at a frequency selected to excite the molecules of the process gas to create a plasma.

The measuring procedure 204 includes measuring the optical emissions from one or more regions of the plasma in the plasma zone 126. For example, the controller 190 can operate the detector 180 to move the sensor head 182 to a first position (shown in solid lines in FIG. 2) at a first distance $D_1$ from a plane defined by the workpiece W. In the first position, the detector 180 measures the optical emissions from a first region $R_1$ of the plasma zone 126 corresponding to the line of sight of the sensor head 182. After measuring the optical emissions at the first position, the detector 180 can move the sensor head 182 to a second position (shown in broken lines in FIG. 2) at a second distance $D_2$ from the workpiece plane. In the second position, the detector 180 measures the optical emissions from a second region $R_2$ of the plasma zone 126 corresponding to the line of sight of the sensor head 182. The controller 190 can subsequently operate the detector 180 to move the sensor head 182 along the window 132 between any number of other positions so that the detector 180 can measure the optical emissions from additional regions of the plasma zone 126. In other embodiments, the detector 180 may include a plurality of sensor heads fixed at different positions across the window 132 to sense the optical emissions from multiple regions of the plasma zone 126 in lieu of or in addition to the movable sensor head 182.

The detector 180 measures the optical emissions at one or more wavelengths from each region of the plasma zone 126. For example, the detector 180 can measure the optical emissions at a first wavelength, a second wavelength, and a third wavelength from each of the first and second regions $R_1$ and $R_2$ when the sensor head 182 is at the first and second positions, respectively. Alternatively, the detector 180 can measure the optical emissions from different regions at different wavelengths. For example, the detector 180 can measure the optical emissions (a) from the first region $R_1$ at a first wavelength and a second wavelength, and (b) from the second region $R_2$ at a third wavelength and a fourth wavelength. In other embodiments, the detector 180 can measure a spectrum from any one of the examined regions of the plasma zone 126. Accordingly, the detector 180 measures the optical emissions at one or more wavelengths from one more regions of the plasma zone 126 during the measuring procedure 204.

The illustrated first calculating procedure 206 includes summing at least some of the wavelength intensities for each region of the plasma zone 126. For example, if the detector 180 measures the optical emissions at the first, second, and third wavelengths from the first region $R_1$ of the plasma zone 126, the controller 190 sums the measured intensities of the three wavelengths to produce a total measured intensity of emissions from the first region $R_1$. This process can be repeated for some or all of the regions of the plasma zone 126 from which optical emissions are measured. In other embodiments, the first calculating procedure 206 may not include summing the intensity of all of the wavelengths measured at each position of the sensor head 182, but rather summing only some of the wavelengths measured at each position. In additional embodiments, the first calculating procedure 206 may not include summing the optical emission intensities measured at each position, but rather the optical emission intensities measured at only some of the positions. Alternatively, if the detector 180 measures only a single wavelength at each position, the method may not include the first calculating procedure 206.

The determining procedure 208 includes determining a distance from the workpiece W at which the boundary of a sheath or dark space of the plasma is located. In several applications, the boundary of a sheath of a plasma is assumed to be located at the distance where the intensity of optical emissions is a predetermined percentage of the peak intensity. For example, the sheath can be assumed to be located at the distance where the intensity is from 70% to 90% of the maximum intensity. Accordingly, in the determining procedure 208, the controller 190 analyzes the summed intensities for each position of the sensor head 182 to determine the peak summed intensity. Next, the controller 190 identifies the distance at which the summed intensity is a predetermined percentage of the maximum summed intensity to determine the thickness of the sheath.

The second calculating procedure 210 includes calculating an ion density and/or other parameter of the plasma based on the determined thickness of the sheath of the plasma. For example, the sheath thickness can be characterized by the following equation of Child-Langmuir Law:

$$J_{ion} = \frac{4}{9}\varepsilon_0 \sqrt{\frac{2q}{M}} \frac{V_0^{3/2}}{s^2} \tag{1}$$

Moreover, the ion current density $J_{ion}$ can also be represented at the sheath edge with the following equation and with a Bohm acoustic speed $\mu_B = (qT_e/M)^{1/2}$:

$$J_{ion} = qn_i\mu_B = qn_i\sqrt{\frac{qT_e}{M}} \tag{2}$$

in which $J_{ion}$ is the ion current density crossing the sheath edge, $\varepsilon_0$ is the free-space permittivity, q is the ion charge, M is the ion mass, $V_0$ is the absolute value of the applied potential, s is the sheath thickness, $n_i$ is the ion density, and $T_e$ is the electron temperature in units of eV. By solving equations (1) and (2) simultaneously, the ion density $n_i$ can be represented by the following equation:

$$n_i = \frac{4}{9}\frac{\varepsilon_0}{q}\sqrt{\frac{2}{T_e}} \frac{V_0^{3/2}}{s^2} \tag{3}$$

In equation (3), the ion density $n_i$ is dependent on the applied voltage $V_0$, the sheath thickness s, and the electron temperature $T_e$. Accordingly, the controller 190 can determine the ion density $n_i$ assuming the applied voltage $V_0$ and electron temperature $T_e$ are known or can be measured by other suitable methods.

In several applications, after determining the ion density or another parameter of the plasma, the controller 190 can operate the power source 125, the energy generator 140, the valve assembly 174, and/or other components of the system 100 to change the plasma parameter(s) so that the parameter(s) is/are within a desired range. Moreover, in addition to or in lieu of changing the plasma parameters, the controller 190 can change the workpiece processing parameters based on the determined plasma parameter. In several embodiments, the method 200 illustrated in FIG. 3 can be repeated periodically or continuously during workpiece processing to monitor a parameter of the plasma.

One feature of operating the system 100 illustrated in FIG. 2 in accordance with the method illustrated in FIG. 3 is that the detector 180 can determine a parameter of the plasma in the chamber 120 based on the optical emissions from the plasma. An advantage of this feature is that, unlike the Langmuir probe, the detector 180 does not draw current from the plasma or cause perturbations in the plasma that can adversely affect workpiece processing and plasma parameter measurement. Another advantage of this feature is that, unlike the Langmuir probe, the detector 180 can accurately measure the plasma parameter even if the system includes a radio-frequency generator or magnetron assembly for generating the plasma.

Another feature of the system 100 illustrated in FIG. 2 is that the detector 180 is positioned external to the chamber 120. An advantage of this feature is that the detector 180 can determine a plasma parameter in real time during workpiece processing. Moreover, because the illustrated detector 180 is positioned outside the chamber 120, the detector 180 does not introduce contamination into the chamber 120 or interfere with the ingress and egress of workpieces from the chamber 120. Furthermore, unlike the Langmuir probe, the detector 180 can measure nonequilibrium plasma, such as glow discharge and steady state plasma with a high voltage pulse, because the sensor head 182 is external to the chamber 120 and not contacted by secondary electrons in the plasma.

D. Several Examples of Data Collected From Different Plasma Processes

Figure 4:
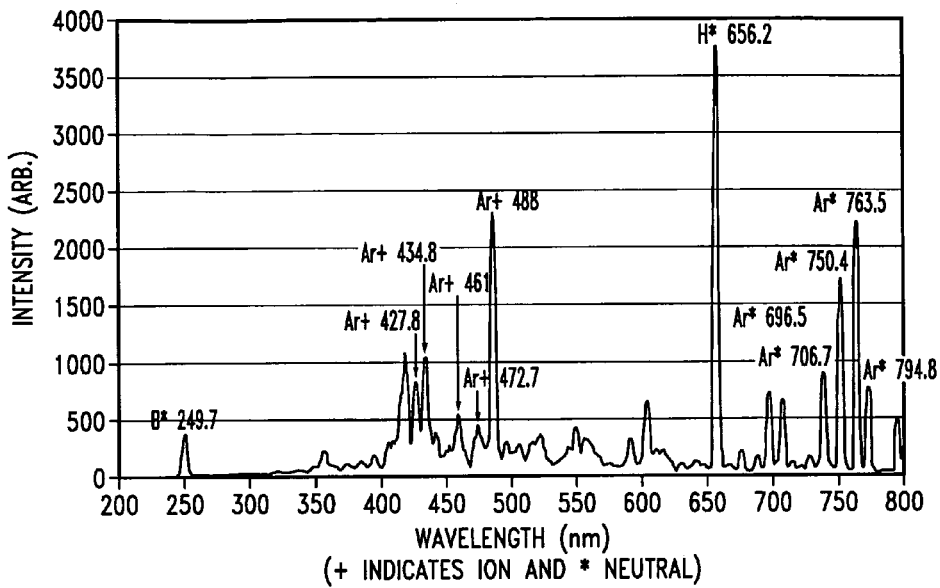
FIG. 4 illustrates the optical emissions spectrum measured at a specific distance from a workpiece during one example of a process performed in accordance with an embodiment of the invention.
Figure 5:
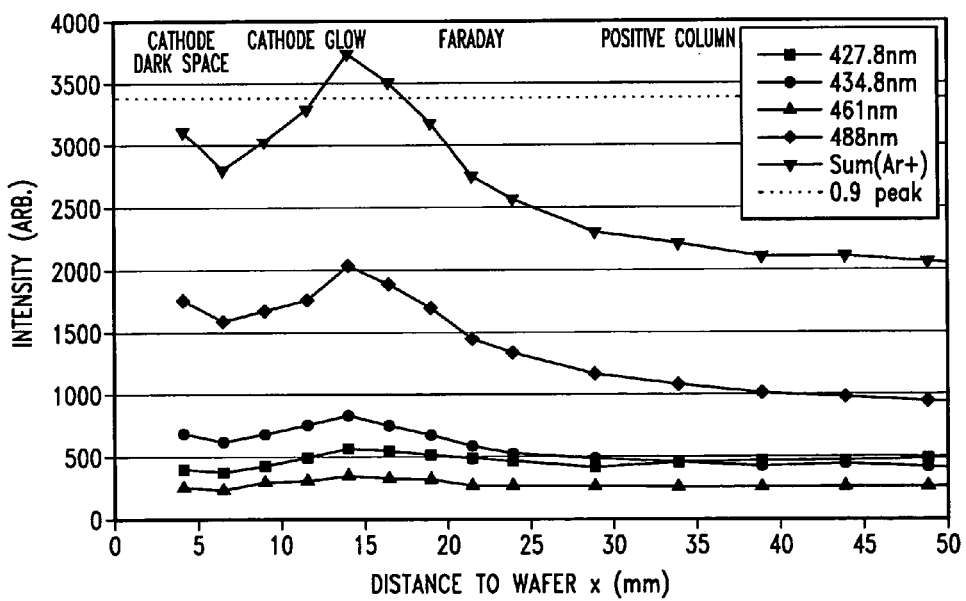
FIG. 5 illustrates the measured intensity of several wavelengths at different distances from the workpiece during one example of a process performed in accordance with an embodiment of the invention.

FIGS. 4-7 are examples of data collected from different plasma processes conducted in accordance with the method 200 described above with reference to FIG. 3. For example, FIGS. 4 and 5 illustrate the data gathered during the measuring and calculating procedures 204 and 206, respectively, of an Argon pulsed mode glow discharge process with a −3 kV pulse potential, a 40 μsec pulse width, a 5 kHz pulse frequency, and a 30 mTorr process pressure. Specifically, FIG. 4 illustrates the optical emissions spectrum measured at a distance of 10 mm from the wafer during the measuring procedure 204. FIG. 5 illustrates the measured intensity of several wavelengths (i.e., 427.8 nm, 434.8 nm, 461 nm, and 488 nm) at different distances from the wafer. The graph also illustrates the summed intensity of the specific wavelengths. As described above, the boundary of the sheath can be determined by identifying the distance at which the measured intensity is approximately 70% to 90% of the maximum measured intensity. Assuming the boundary of the sheath is located at the distance where the intensity is 90% of the maximum summed intensity, the boundary of the sheath in this plasma process is located approximately 12 mm from the wafer. In this specific process, the electron temperature ($T_e$=1.47 eV) can be obtained from a separate Langmuir probe measurement. Based on the measured sheath thickness (s=12 mm), the applied voltage ($V_0$=3 kV), and the electron temperature ($T_e$=1.47 eV), the ion density ($n_i$=3.27×10$^{10}$/cm$^3$) can be calculated from equation (3).

Figure 6:
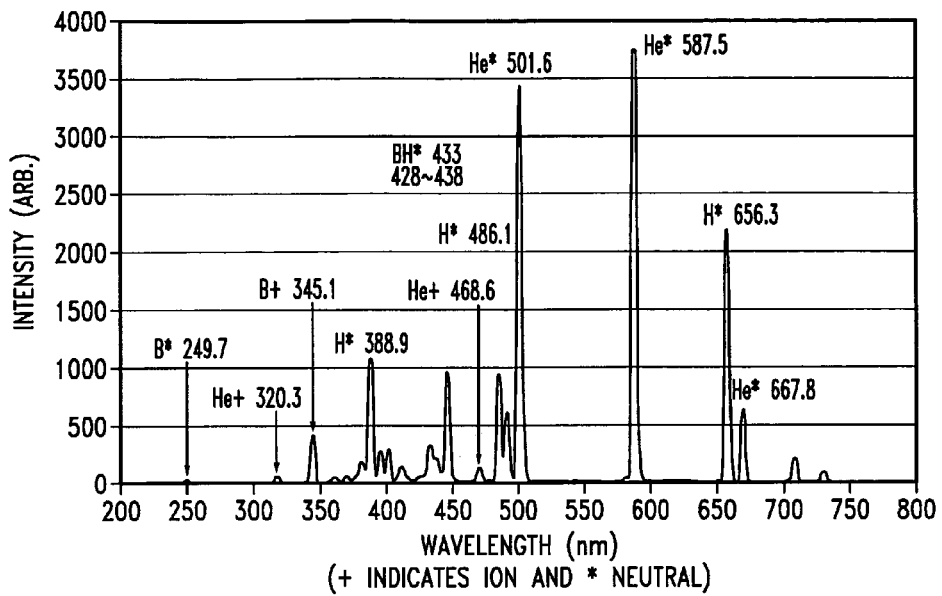
FIG. 6 illustrates the optical emissions spectrum measured at a specific distance from a workpiece during an example of another process performed in accordance with an embodiment of the invention.
Figure 7:
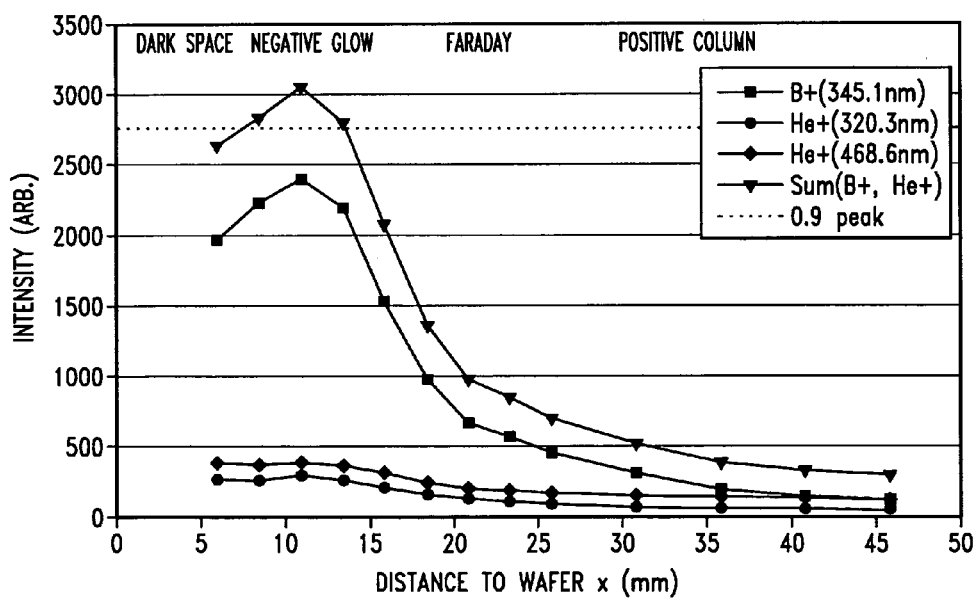
FIG. 7 illustrates the measured intensity of several wavelengths at different distances from the workpiece during an example of another process performed in accordance with an embodiment of the invention.

FIGS. 6 and 7 illustrate the data gathered during the measuring and calculating procedures 204 and 206, respectively, of a $B_2H_6$/He (5/95) pulsed glow discharge process with a −6 kV pulse potential, a 40 μsec pulse width, a 5 kHz pulse frequency, and a 155 mTorr process pressure. Specifically, FIG. 6 illustrates the optical emissions spectrum measured at a distance of 26 mm from the wafer during the measuring procedure 204. FIG. 7 illustrates the measured intensity of several wavelengths (i.e., 345.1 nm, 320.3 nm, and 468.6 nm) at different distances from the wafer. The graph also illustrates the summed intensity of the specific wavelengths. Assuming the boundary of the sheath is located at the distance where the intensity is 90% of the maximum summed intensity, the boundary of the sheath in this plasma process is located approximately 7.7 mm from the wafer. In this specific process, the electron temperature ($T_e$=9.7 eV) can be obtained from a separate Langmuir probe measurement. However, because the process pressure is 155 mTorr, equation (1), which is a collisionless version of the Child-Langmuir Law, may not be valid. Specifically, assuming that the charge transfer collision of $B^+/He^+$ with He neutral dominates, the mean free path $\lambda_i$ of the charge transfer collision of $B_2H_6/He$ is approximately 1 mm. Consequently, the collisionless condition is not valid due to the ratio s/$\lambda_i$~7.7>>1. A constant ion cross-section collisional version of the Child-Langmuir Law, which is expressed by the following equation, can be used to characterize the intermediate pressure regime:

$$J_{ion} = \sqrt{\frac{500}{243\pi}} \varepsilon_0 \sqrt{\frac{2q\lambda_i}{M}} \frac{V_0^{3/2}}{s^{5/2}} \quad (4)$$

in which $\lambda_i$ is a mean free path of the charge transfer collision and is approximately 1 mm when the pressure of $B_2H_6/He$ (5/95) plasma is 155 mTorr assuming a cross section of the charge transfer collision $\sigma_i$~$2\times10^{-15}$ cm$^2$. Based on equation (4) and the above-noted assumption, the plasma density ($n_i$=$5.74\times10^{10}$/cm$^3$) can be calculated.

From the foregoing, it will be appreciated that specific embodiments of the invention have been described herein for purposes of illustration, but that various modifications may be made without deviating from the spirit and scope of the invention. For example, although the illustrated methods describe the calculation of ion density, the system can be used to measure other plasma parameters. Accordingly, the invention is not limited except as by the appended claims.

We claim:

1. A method of processing a microfeature workpiece, comprising:
   generating a plasma in a chamber while a microfeature workpiece is positioned in the chamber;
   measuring optical emissions from the plasma; and
   determining a parameter of the plasma based on the measured optical emissions, wherein:
   measuring optical emissions from the plasma comprises (a) determining an intensity of the optical emissions at a plurality of discrete wavelengths from a first region of the plasma spaced apart from the microfeature workpiece by a first distance, and (b) determining an intensity of the optical emissions at the plurality of discrete wavelengths from a second region of the plasma spaced apart from the microfeature workpiece by a second distance different than the first distance; and
   determining the parameter of the plasma comprises (a) summing at least some of the determined intensities of the discrete wavelengths from the first region, and (b) summing at least some of the determined intensities of the discrete wavelengths from the second region.

2. The method of claim 1 wherein determining the parameter of the plasma comprises estimating a dimension of a sheath of the plasma.

3. The method of claim 1 wherein determining the parameter of the plasma comprises calculating an ion density.

4. The method of claim 1 wherein:
   determining the parameter of the plasma comprises determining a distance from the workpiece at which the intensity of the optical emissions is a predetermined percentage of a maximum determined intensity.

5. The method of claim 1 wherein
   determining the parameter of the plasma comprises (a) estimating a dimension of a sheath of the plasma by determining a distance from the workpiece at which the intensity of the optical emissions is a predetermined percentage of a maximum determined intensity, and (b) calculating an ion density based on the estimated dimension of the sheath.

6. The method of claim 1, further comprising applying material to the microfeature workpiece while determining the parameter of the plasma.

7. The method of claim 1 wherein determining the parameter of the plasma comprises estimating the parameter of the plasma without placing a sensor in the chamber.

8. The method of claim 1 wherein measuring optical emissions from the plasma comprises sensing optical emissions from the plasma with a detector positioned external to the chamber.

9. The method of claim 1, further comprising controlling the parameter of the plasma in response to the measured optical emissions.

10. A method of processing a microfeature workpiece, comprising:
    generating a plasma in a chamber;
    depositing material onto a microfeature workpiece in the chamber; and
    monitoring in real time a parameter of the plasma in the chamber while depositing material onto the microfeature workpiece, wherein monitoring in real time the parameter of the plasma comprises:
    measuring an intensity of optical emissions at a plurality of discrete wavelengths from a first region of the plasma spaced apart from the microfeature workpiece by a first distance;
    measuring an intensity of optical emissions at the plurality of discrete wavelengths from a second region of the plasma spaced apart from the microfeature workpiece by a second distance different than the first distance; and
    estimating a dimension of a sheath of the plasma based on at least one of (a) at least some of the measured intensities of the discrete wavelengths from the first region, and (b) at least some of the measured intensities of the discrete wavelengths from the second region.

11. The method of claim 10 wherein depositing material onto the microfeature workpiece comprises implanting ions in the workpiece.

12. The method of claim 10 wherein depositing material onto the microfeature workpiece comprises depositing molecules onto the workpiece via plasma enhanced physical vapor deposition.

13. The method of claim 10 wherein depositing material onto the microfeature workpiece comprises depositing molecules onto the workpiece via plasma enhanced chemical vapor deposition.

14. The method of claim 10 wherein depositing material onto the microfeature workpiece comprises applying an etchant to the workpiece.

15. The method of claim 10 wherein monitoring in real time the parameter of the plasma comprises:
   determining a distance from the microfeature workpiece at which the intensity of the optical emissions is a predetermined percentage of a maximum measured intensity.

16. A method of processing a microfeature workpiece, comprising:
   generating a plasma in a chamber;
   measuring a first intensity of optical emissions at a first wavelength and a second intensity of optical emissions at a second wavelength from a first region of the plasma spaced apart from the microfeature workpiece by a first distance, the first wavelength being different than the second wavelength;
   measuring a third intensity of optical emissions at the first wavelength and a fourth intensity of optical emissions at the second wavelength from a second region of the plasma spaced apart from the microfeature workpiece by a second distance different than the first distance; and
   estimating a dimension of a sheath of the plasma based on at least some of the measured first and second intensities from the first region and the measured third and fourth intensities from the second region.

17. The method of claim 16 wherein estimating a dimension of a sheath of the plasma includes summing the first and second intensities to produce a first total intensity of the first region and summing the third and fourth intensities to produce a second total intensity of the second region.

18. The method of claim 16 wherein estimating a dimension of a sheath of the plasma includes
   summing the first and second intensities to produce a first total intensity of the first region;
   summing the third and fourth intensities to produce a second total intensity of the second region; and
   determining a distance from the microfeature workpiece at which a boundary of the sheath is located based on the first and second total intensities.

19. The method of claim 16 wherein estimating a dimension of a sheath of the plasma includes
   summing the first and second intensities to produce a first total intensity of the first region;
   summing the third and fourth intensities to produce a second total intensity of the second region;
   determining a peak intensity based on the first and second total intensities; and
   determining a distance from the microfeature workpiece at which an intensity of optical emissions is at a predetermined percentage of the peak intensity.

20. The method of claim 19 wherein determining a distance includes determining a distance from the microfeature workpiece at which an intensity of optical emissions is at about 70% to about 90% of the peak intensity.

21. The method of claim 16, further comprising calculating an ion density of the plasma according to the following formula:

$$n_i = \frac{4}{9}\frac{\varepsilon_0}{q}\sqrt{\frac{2}{T_e}}\frac{V_0^{3/2}}{s^2}$$

in which $N_i$ is the ion density, $\varepsilon_0$ is the free-space permittivity, q is the ion charge, $V_0$ is the absolute value of an applied potential, s is the sheath thickness, and $T_e$ is the electron temperature in units of eV.

22. The method of claim 16, further comprising depositing material onto the microfeature workpiece while measuring at least one of the first, second, third, and fourth intensities.

23. The method of claim 16, further comprising depositing molecules onto the workpiece via plasma enhanced physical vapor deposition while measuring at least one of the first, second, third, and fourth intensities.

24. The method of claim 16, further comprising depositing molecules onto the workpiece via plasma enhanced chemical vapor deposition while measuring at least one of the first, second, third, and fourth intensities.

25. The method of claim 16, further comprising applying an etchant to the workpiece while measuring at least one of the first, second, third, and fourth intensities.

* * * * *

UNITED STATES PATENT AND TRADEMARK OFFICE
CERTIFICATE OF CORRECTION

PATENT NO. : 7,476,556 B2 Page 1 of 1
APPLICATION NO. : 11/201668
DATED : January 13, 2009
INVENTOR(S) : Shu Qin et al.

It is certified that error appears in the above-identified patent and that said Letters Patent is hereby corrected as shown below:

In column 10, line 51, in Claim 10, delete "region." and insert -- region, --, therefor.

In column 12, line 21, in Claim 21, delete "$N_i$" and insert -- $n_i$ --, therefor.

Signed and Sealed this

Twelfth Day of May, 2009

JOHN DOLL
*Acting Director of the United States Patent and Trademark Office*